US012514305B2

(12) United States Patent
Thor et al.

(10) Patent No.: US 12,514,305 B2
(45) Date of Patent: Jan. 6, 2026

(54) LEG GARMENT WITH ADJUSTABLE SUPPORT ELEMENTS

(71) Applicant: Tighties Inc, Coronado, CA (US)

(72) Inventors: Arni Thor, Coronado, CA (US); Shireen Maria Thor, Coronado, CA (US)

(73) Assignee: Tighties, Inc., Coronado, CA (US)

( * ) Notice: Subject to any disclaimer, the term of this patent is extended or adjusted under 35 U.S.C. 154(b) by 436 days.

(21) Appl. No.: 18/163,259

(22) Filed: Feb. 1, 2023

(65) Prior Publication Data

US 2023/0240386 A1 Aug. 3, 2023

Related U.S. Application Data

(60) Provisional application No. 63/305,433, filed on Feb. 1, 2022.

(51) Int. Cl.

*A41D 1/08* (2018.01)
*A61F 5/01* (2006.01)

(Continued)

(52) U.S. Cl.

CPC .............. *A41D 1/08* (2013.01); *A61F 5/0123* (2013.01); *A61H 1/00* (2013.01); *A61H 3/00* (2013.01)

(58) Field of Classification Search

CPC ........ A61F 5/0123; A61F 5/0104; A61F 5/01; A61F 5/06; A61F 5/03; A61F 5/30;

(Continued)

(56) References Cited

U.S. PATENT DOCUMENTS

| | | | |
|---|---|---|---|
| 4,089,064 | A | 5/1978 | Chandler |
| 4,216,547 | A | 8/1980 | Picchione |

(Continued)

FOREIGN PATENT DOCUMENTS

| | | | |
|---|---|---|---|
| CN | 1806706 | A | 7/2006 |
| EP | 1323397 | A2 | 7/2003 |

(Continued)

OTHER PUBLICATIONS

WO 2011087048, published Jul. 21, 2011, English translation provided.

(Continued)

*Primary Examiner* — Daniel A Miller
(74) *Attorney, Agent, or Firm* — David J. Thibodeau, Jr.; VLP Law Group LLP

(57) ABSTRACT

The present invention is directed at a series of leg garments that provide support for reducing loads at the knee, hip, ankle, and spine, as well as options for leg shape contouring, muscle training, pain reduction, and injury treatment. The leg garments may comprise a base layer with reinforced portions disposed throughout. The leg garments may comprise adjustable support elements. The size, shape, position, quantity, and material composition of the reinforced portions and the adjustable support elements may be selected to achieve the desired tensive properties for the leg garment. Various tensioning mechanisms may be positioned at strategic areas to further control the leg garments' tensive properties, improving effectiveness and comfort. In some embodiments, cables may run through channels in the reinforced portions or support elements.

21 Claims, 13 Drawing Sheets

(51) Int. Cl.
*A61H 1/00* (2006.01)
*A61H 3/00* (2006.01)

(58) Field of Classification Search
CPC ........ A61F 5/0125; A61F 5/02; A61F 5/0109; A61F 2005/0137; A61H 1/00; A61H 3/00; A61H 2201/0025; A61H 2201/165; A41B 9/001; A41B 9/14
USPC .......................................................... 602/62
See application file for complete search history.

(56) References Cited

U.S. PATENT DOCUMENTS

| | | | |
|---|---|---|---|
| 5,263,923 A | 11/1993 | Fujimoto | |
| 5,628,725 A | 5/1997 | Ostergard | |
| 5,925,010 A | 7/1999 | Caprio | |
| 6,186,970 B1 | 2/2001 | Fujii et al. | |
| 7,198,610 B2 | 4/2007 | Ingimundarson et al. | |
| 7,615,021 B2 | 11/2009 | Nordt, III et al. | |
| 7,615,027 B2 | 11/2009 | Nordt, III et al. | |
| 7,637,884 B2 | 12/2009 | Nordt, III et al. | |
| 7,785,281 B2 | 8/2010 | Scott | |
| 7,814,576 B2 | 10/2010 | Nakazawa | |
| 7,959,591 B2 | 6/2011 | Powers et al. | |
| 8,007,457 B2 | 8/2011 | Taylor | |
| 8,296,864 B2 | 10/2012 | Torry | |
| 8,341,772 B1 | 1/2013 | Flores | |
| 8,533,864 B1 | 9/2013 | Kostrzewski | |
| 8,808,211 B2 | 8/2014 | Paulos et al. | |
| 8,852,133 B2 | 10/2014 | Paulos et al. | |
| 9,320,634 B2 | 4/2016 | Paulos | |
| 9,327,156 B2 | 5/2016 | von Hoffmann et al. | |
| 9,345,275 B2 | 5/2016 | Albin et al. | |
| 9,468,554 B2 | 10/2016 | Petursson et al. | |
| 9,554,934 B2 | 1/2017 | Paulos et al. | |
| 9,895,569 B2 | 2/2018 | Yao | |
| 10,051,897 B2 | 8/2018 | Freddi et al. | |
| 10,675,166 B2 | 6/2020 | Paulos et al. | |
| 10,786,381 B2 | 9/2020 | Paulos et al. | |
| 11,259,948 B2 | 3/2022 | Ingimundarson et al. | |
| 11,484,425 B2 | 11/2022 | Eberwien | |
| 11,484,426 B2 | 11/2022 | Thor et al. | |
| 11,857,448 B2 | 1/2024 | Thor | |
| 2008/0208092 A1 | 8/2008 | Sawa | |
| 2009/0287128 A1 | 11/2009 | Ingimundarson et al. | |
| 2014/0174454 A1 | 6/2014 | Naef | |
| 2017/0354526 A1 | 12/2017 | Li | |
| 2018/0049903 A1 | 2/2018 | Witherspoon et al. | |
| 2019/0082751 A1 | 3/2019 | Young | |
| 2019/0105216 A1* | 4/2019 | Chin | A61H 3/00 |
| 2020/0146866 A1 | 5/2020 | Eberwein et al. | |
| 2020/0211531 A1 | 7/2020 | Kumar et al. | |
| 2021/0045930 A1 | 2/2021 | Carrillo et al. | |
| 2021/0361456 A1 | 11/2021 | Rutckyj et al. | |
| 2022/0022567 A1 | 1/2022 | Rutckyj et al. | |
| 2024/0008563 A1 | 1/2024 | Weber-Unger | |

FOREIGN PATENT DOCUMENTS

| | | |
|---|---|---|
| JP | 4607233 B1 | 1/2011 |
| WO | 2011087048 A1 | 7/2011 |

OTHER PUBLICATIONS

EP 132339, granted Jul. 2, 2003, English translation provided.
CN 1806706, granted Jul. 26, 2006, English translation provided.

* cited by examiner

LEG GARMENT WITH ADJUSTABLE SUPPORT ELEMENTS

CROSS-REFERENCE TO RELATED APPLICATIONS

This application claims the benefit of U.S. provisional patent application No. 63/305,433, titled "ORTHOPEDIC GARMENTS" and filed on Feb. 1, 2022, the content of which is incorporated by reference in its entirety.

BACKGROUND

The present disclosure relates generally to the field of leg garments, and, in particular, to leg garments with support elements for leg and lower extremity shape contouring, muscle training, pain reduction, and injury prevention and treatment.

SCOPE OF THE PRIOR ART

The knee is particularly vulnerable to injury which leads to pain, swelling, disability, and reduction in quality of life. It is the joint between the two longest bones of the body, and the entire weight of the body is transferred to the foot through the knee. The knee is also more prone to injury because its stability decreases as it bends. The menisci and the ligaments provide less effective support to the bent knee.

Most sports require walking or running, or some other similar motion like skating, as a component. These sports may require movements that cause lateral shifting of the knee joint (i.e., which may be the femur and tibia shifting relative to one another in opposite directions laterally to the normal plane of motion for the knee joint, or the femur and tibia shifting together laterally to the normal plane of motion of the knee joint), which can lead to injury. Injury to the joint can be acute or chronic but both conditions can be debilitating due to the pain it causes that often leads to reduced activity that further destabilizes the overall system and often causes other complications such as weight gain and depression.

Staying active has been shown to improve overall health, both physical and mental and strong, pliable muscles reduce the likelihood of injury, improve overall posture and health and make people feel better about themselves. The reality however is that many people are very limited in their time to work out to strengthen their muscles and their activity level gradually goes down. Having an exercise equipment built into clothing for people on the go has been missing, not just for the average user but also for the trainer that wants to train athletes to engage certain muscles in a different way.

Various approaches have been taken to reduce loads inside the knee, reduce pain and/or reduce lateral knee shifting and risk of resultant knee injury or other types of lower extremity injury. For example, many athletes wear neoprene sleeves around their knees. These sleeves usually cover the entire knee joint area and have the shortcoming of restricting movement. Also, some athletes wear knee braces that have rigid articulating members on the outside of the knees. These braces are cumbersome and also limit movement. Other approaches have suggested garments that mimic taping for providing support. These garments however are limited in the stability that they provide since there is minimal or no adjustability allowed to the support and with enhanced support it becomes too difficult to apply the garment. Other approaches have suggested unloader knee bracing to relief pain for people with osteoarthritis of the knee. These knee braces however are complicated to use, often bulky and uncomfortable but also require a certified health care professional to fit and bill the insurance company excessive amount of money. Secondly there is exercise and strengthening which is the most common method to prevent these sorts of injuries however most often conventional exercise and training involve movements that occur outside of the actual environment that cause the type of injury such as soccer or other types of sports. Very few options exist that allow the therapist to train certain muscle groups specifically during activity other than using elastic bands which also significantly restrict the athlete's overall ability to move. Lastly, the day-to-day muscle engagement and training requirement needs options to allow people on the go to continue to work out without having to spend a lot of money and time getting to and from the gym.

The present invention endeavors to provide a garment that provides an adjustable and variable enhanced support for reducing loads at the knee, hip, ankle and spine as well as an option for promoting muscle strengthening and training during actual activity or play, which is also easy to apply and adjust. This same garment can have adjustable and non adjustable support structures built in but also sensors, metal, plastic and carbon fiber.

SUMMARY

The present disclosure satisfies the foregoing needs by providing, inter alia, a leg garment for addressing each of the foregoing desirable traits as well as methods of their manufacture and methods of their use.

A first aspect of the present disclosure is directed at a leg garment. The leg garment may comprise a base layer extending down from a waist, where a hip portion, medial thigh portions, and calf portions of the base layer are reinforced to have an increased resistance to stretching. A first pair of sagitally mirrored anchor points may be positioned on the hip portion or the medial thigh portions. A second pair of sagitally mirrored anchor points positioned on the medial thigh portions or the calf portions.

A first support element may have a first end attached to one of the reinforced portions of the base layer. The second end of the first support element may attach to one of the first-pair sagitally mirrored anchor points. The first-pair of sagitally mirrored anchor points may be first-pair tensioning mechanisms. A path of the first support element may span from one of the hip portions to one of the medial thigh portions and may spiral around a hip.

A second support element may have a first end attached to one of the reinforced portions of the base layer. The second end of the second support element may attach to one of the second-pair sagitaly mirrored anchor points. The second-pair of sagitally mirrored anchor points may be second-pair tensioning mechanisms. A path of the second support element may span from one of the medial thigh portions to one of the calf portions and may spiral around a leg.

A first catch positioned along the path of the first support element may be configured to catch the second end of the first support element when the first support element is not attached to one of the first-pair of sagitally mirrored anchor points or when the first support element is at a minimum tension.

A second catch positioned along the path of the second support element may be configured to catch the second end of the second support element when the second support element is not attached to one of the second-pair of sagitally mirrored anchor points or when the second support element is at a minimum tension.

A first cover may extend from the first end of the first support element to the first catch and may enclose the first support element and a portion of the base layer surrounding the first support element.

A second cover may extend from the first end of the second support element to the second catch and may enclose the second support element and a portion of the base layer surrounding the second support element.

A second aspect of the present disclosure is directed at a support element for use with the leg garment. A cable may run the length of the support element and may limit the maximum stretch distance of support element.

A third aspect of the present disclosure is directed at a cable system for use with the leg garment. The cable system may comprise channels disposed within the base layer and cables may run through the channels.

BRIEF DESCRIPTION OF THE DRAWINGS

The foregoing summary, as well as the following detailed description of preferred variations of the invention, will be better understood when read in conjunction with the appended drawings. For the purpose of illustrating the invention, there is shown in the drawings variations that are presently preferred. It should be understood, however, that the invention is not limited to the precise arrangements shown. In the drawings, where.

DETAILED DESCRIPTION

Implementations of the present technology will now be described in detail with reference to the drawings, which are provided as illustrative examples so as to enable those skilled in the art to practice the technology. Notably, the figures and examples described below are not meant to limit the scope of the present disclosure to any single implementation or implementations, but other implementations are possible by way of interchange of, substitution of, or combination with some or all of the described or illustrated elements. Wherever convenient, the same reference numbers will be used throughout the drawings to refer to same or like parts.

Moreover, while embodiments described herein are primarily discussed in the context of leg garments for leg shape contouring, muscle training, pain reduction, and injury treatment, it will be recognized by those of ordinary skill that the present disclosure is not so limited. In fact, the principles of the present disclosure described herein may be readily applied to other parts of the anatomy of a human. For example, many common injuries, such as a partial or complete tear of a tendon (e.g., a biceps tendon, a triceps tendon, an Achilles tendon, and the like), may require an individual to rest the injured tendon, whether surgical or non-surgical treatment is required. Accordingly, the principles described herein may be readily adapted for use with other portions of the anatomy. For example, the garments described herein may be readily adapted for use on the arm, elbow, shoulder, ankle, etc., where movement, whether in extension, flexion, adduction, abduction, internal rotation, or external rotation, may need to be constrained in order to facilitate recovery from, for example, an injury or other medical condition, as well as to reduce pain or to help provide bio feedback to train muscles in order to prevent future injuries.

The leg garments described herein provide various benefits to the wearer such as: 1. Reduced muscle fatigue, 2. Strain prevention, 3. A lower risk of muscle soreness, 4. Improved perceived exertion, 5. Increased power & Better jumping ability, 6. Better muscle oxygenation, 7. Comfort, 8. Improved strength recovery, 9. Better recovery after strenuous exercise.

By altering the elasticity of the garment in certain areas, one can impact muscle activation and movement, as well as change the loads on muscles, joints and tendons. By integrating adjustable cables and straps that cross a join into the garment, one can further achieve the same goals of dynamically impacting muscle activation and movement as well to change the loads on muscles, joints and tendons. Furthermore, by externally applying adjustable or nonadjustable straps and cables as well as rigid structures, one can achieve maximum level of support in a garment. The present invention focuses on all of the above elements.

Figure 1A:
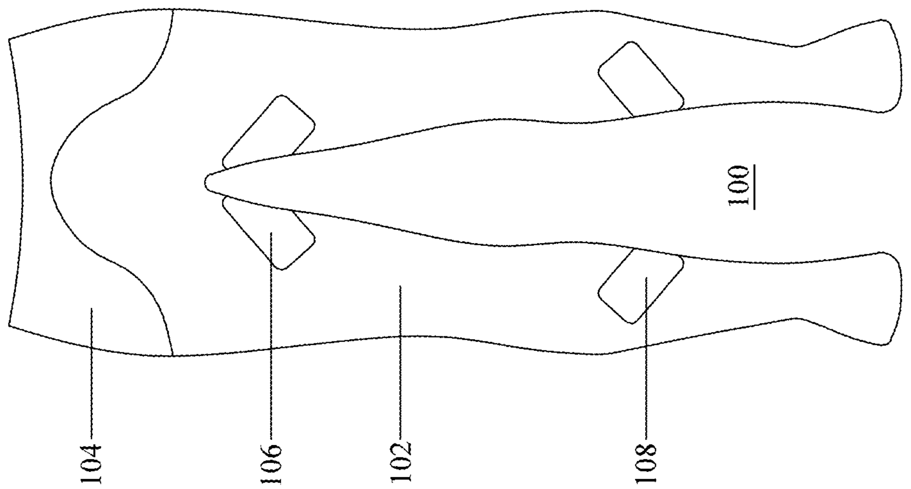
FIG. 1*a* is a front view of a leg garment, according to an embodiment.
Figure 1B:
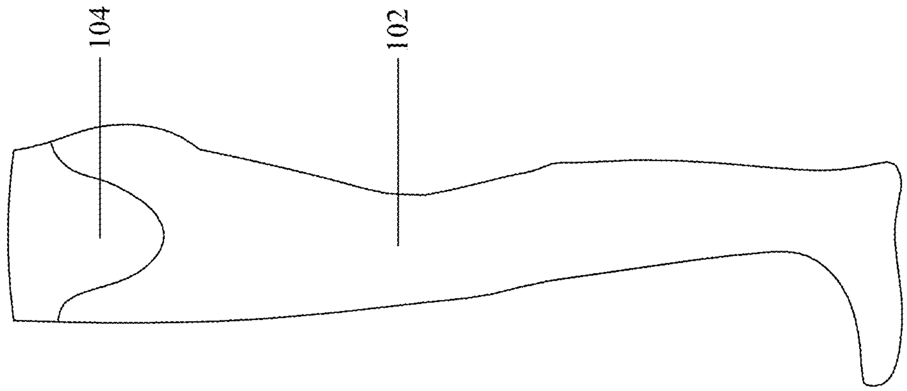
FIG. 1*b* is a right outside view of the leg garment of FIG. 1*a*.
Figure 1C:
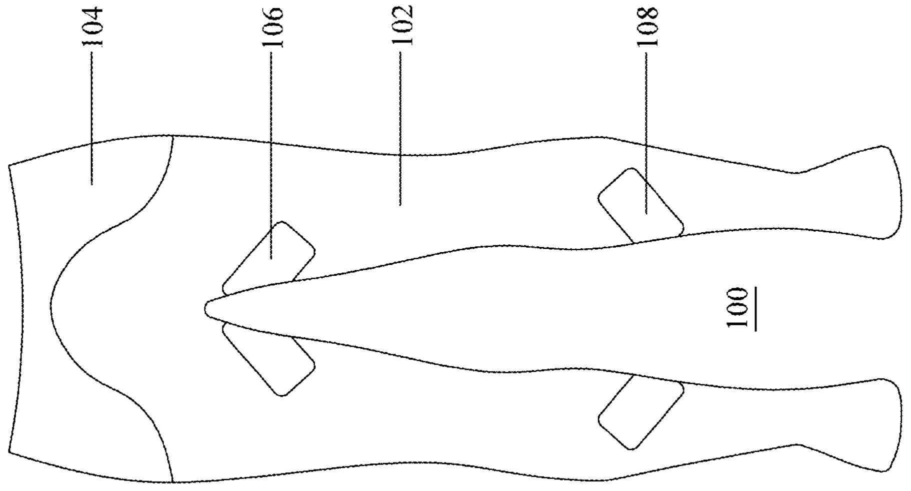
FIG. 1*c* is a back view of the leg garment of FIG. 1*a*.

FIGS. 1*a*-1*c* show a leg garment 100, according to an embodiment. Specifically, FIG. 1*a* is front view of the leg garment 100, FIG. 1*b* is an outside right view of the leg garment 100, and FIG. 1*c* is a back view of the leg garment 100.

A base layer 102 extends down from a wearer's waist to above a wearer's ankles, or, alternatively, to below the ankle and around the foot, either partially or completely. The base layer 102 may be weakly elastic such that the base layer 102 weakly resists stretching under tensile forces. Preferred materials for the base layer 102 include spandex or other weakly elastic materials.

A hip portion 104, thigh portions 106, and calf portions 108 of the base layer 102 are reinforced to have an increased resistance to stretching. The reinforced portions may be strongly elastic such that the reinforced portions strongly resist stretching under tensile forces. Preferred materials for the reinforced portions include nylon, other strongly elastic materials, or materials with no elastic properties and can contain low or moderate or high flexural modulus.

The hip portion 104, thigh portions 106, and calf portions 108 of the base layer 102 may be reinforced by disposing strongly elastic or inelastic materials into the base layer 102 through sewing or adhesives, as well as through other common physical or chemical means known in the art. Alternatively, the hip portion 104, thigh portions 106, and calf portions 108 of the base layer 102 may be reinforced by gluing a polyurethane film or silicone onto the base layer 102 to create strongly elastic or inelastic areas. The reinforced portions of the base layer 102 may be thinner than non-reinforced portions of the base layer 102 such that the reinforced portions act as shallow grooves in the leg garment 102.

The hip portion 104 is positioned on the hips. The hip portion 104 may fully encircle the waistline of the leg garment 102. Alternatively, the hip portion 104 may be split into two hip portions positioned laterally on the hips.

The two thigh portions 106 are positioned medially on the thighs. Alternatively, the two thigh portions 106 may fully encircle thighs of the leg garment 102.

The two calf portions 108 are positioned medially on the calves. Alternatively, the two calf portions 108 may fully encircle calves of the leg garment 102.

Figures 2A, 2B:
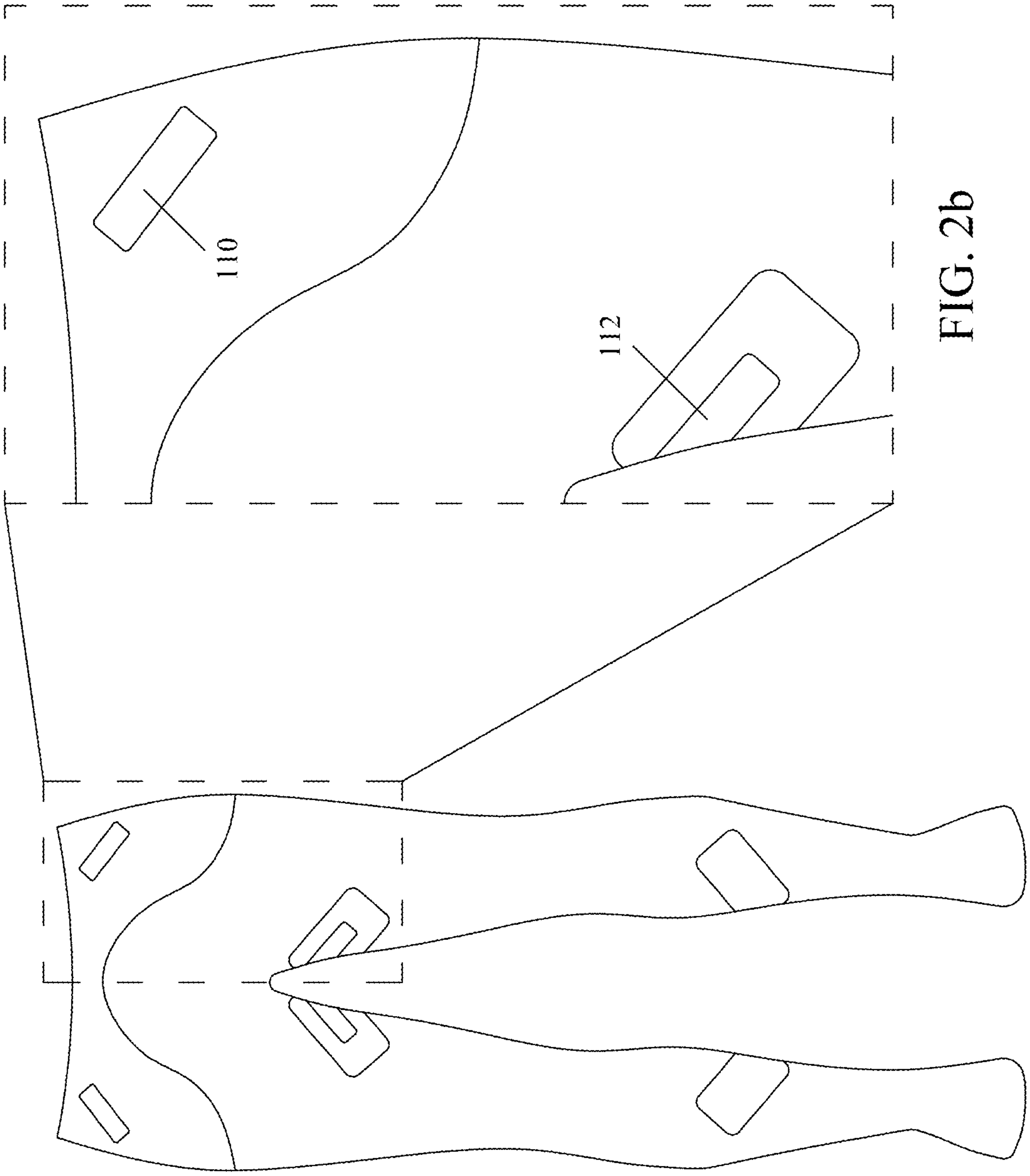
FIG. 2*a* is a front view of a leg garment with anchor points, according to an embodiment.
FIG. 2*b* is an enlarged fragmentary view of the leg garment of FIG. 2*a*.

FIGS. 2*a*-2*b* show a leg garment 100 with anchor points, according to an embodiment. Specifically, FIG. 2*a* is a front view of the leg garment 100 and FIG. 2*b* is an enlarged fragmentary view of the leg garment 200.

A first pair of sagitally mirrored anchor points 110 are positioned on the hip portion 104 of the leg garment 100. Alternatively, the first-pair of sagitally mirrored anchor points 110 may be positioned on the thigh portions 106 of the leg garment. Yet alternatively, the first-pair of sagitally mirrored anchor points 110 includes only one anchor point on one side of the leg garment 100.

A second pair of sagitally mirrored anchor points 112 are positioned on the thigh portions 106 of the leg garment 100. Alternatively, the second-pair sagitally mirrored anchor points 112 may be positioned on the calf portions 108 of the leg garment. Yet alternatively, the second-pair sagitally mirrored anchor points 112 includes only one anchor point on one side of the leg garment 100.

Each of anchor points comprises a loop portion of a hook and loop fastener. Alternatively, each of the anchor points may comprise one part of any two-part fastening mechanism such as one part of a snap fastener or one part of a magnet pair.

Figure 3A:
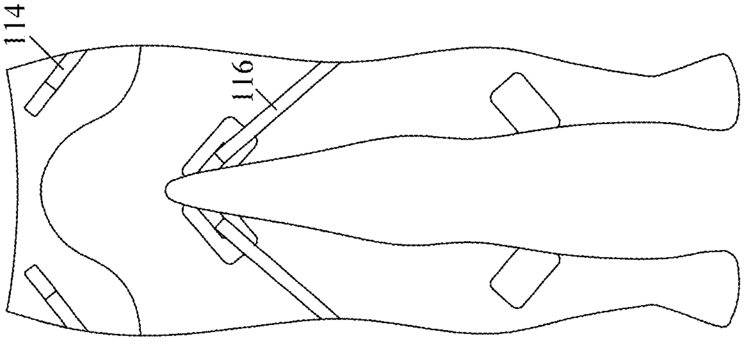
FIG. 3*a* is a front view of a leg garment with support elements, according to an embodiment.
Figure 3B:
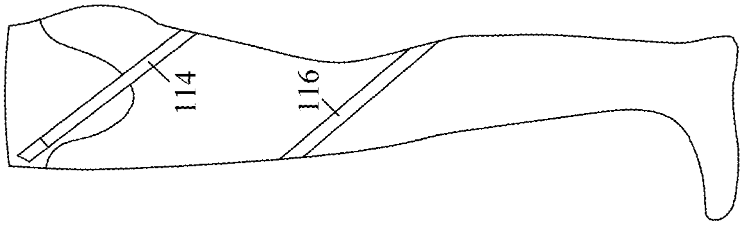
FIG. 3*b* is a right outside view of the leg garment of FIG. 3*a*.
Figure 3C:
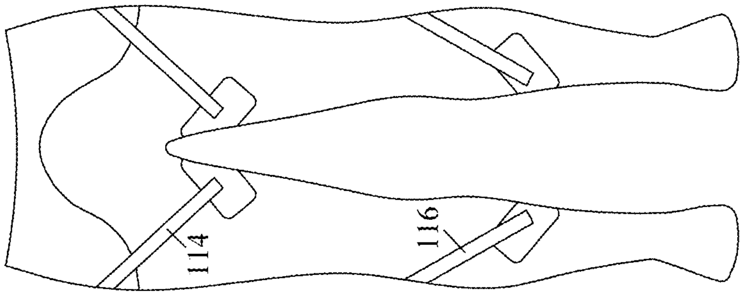
FIG. 3*c* is a back view of the leg garment of FIG. 3*a*.

FIGS. 3*a*-3*c* show a leg garment 100 with support elements, according to an embodiment. Specifically, FIG. 3*a* is front view of the leg garment 100, FIG. 3*b* is an outside right view of the leg garment 100, and FIG. 3*c* is a back view of the leg garment 100.

A first pair of support elements 114 each have first and second ends. The first end of each first-pair support element 114 is attached to the hip portion 104 or one of the thigh portions 106. The second end of each first-pair support element 114 comprises a hook portion of a hook and loop fastener and attaches to one of the first-pair sagitally mirrored anchor points 110. Alternatively, the second end of each first-pair support element 114 may comprise one part of any two-part fastening mechanism such as one part of a snap fastener or one part of a magnet pair.

A path of each first-pair support element 114 starts on an anterior portion of the hip portion 104, spirals around a hip, and ends on a posterior portion of one of the thigh portions 106. The first-pair support element 114 on the right leg spirals clockwise and the first-pair support element 114 on the left leg spirals counter-clockwise when viewed from above.

A distance in between the second end of each first-pair support element 114 and one of the of the first-pair sagitally mirrored anchor points 110 is adjustable. Alternatively, the distance in between the second end of each first-pair support element 114 and one of the of the first-pair sagitally mirrored anchor points 110 may be fixed.

A second pair of support elements 116 each have first and second ends. The first end of each second-pair support element 116 is attached to one of the thigh portions 106 or one of the calf portions 108. The second end of each second-pair support element 116 comprises a hook portion of a hook and loop fastener and attaches to one of the second-pair sagitally mirrored anchor points 112. Alternatively, the second end of each second-pair support element 116 may comprise one part of any two-part fastening mechanism such as one part of a snap fastener or one part of a magnet pair.

A path of each second-pair support element 116 starts on an anterior portion of one of the thigh portions 106, spirals around a leg, and ends on a posterior portion of one of the calf portions 108. The second-pair support element 116 on the right leg spirals clockwise and the second-pair support element 116 on the left leg spirals counter-clockwise when viewed from above.

A distance in between the second end of each second-pair support element 116 and one of the of the second-pair sagitally mirrored anchor points 112 is adjustable. Alternatively, the distance in between the second end of each second-pair support element 316 and one of the of the second-pair sagitally mirrored anchor points 112 may be fixed.

The first-pair and second-pair support elements are straps that are substantially flat in order to more evenly distribute compressive forces over the base layer. Alternatively, the first-pair and second-pair support elements may be cables.

The first-pair and second-pair support elements are strongly elastic such that the first-pair and second-pair support elements strongly resist stretching under tensile forces. Preferred materials for the first-pair and second-pair support elements include nylon or other strongly elastic materials. Alternatively, the first-pair and second-pair support elements are inelastic. Yet alternatively, a majority portion of a support element is inelastic and a minority portion of the support element is weakly elastic or strongly elastic.

Figure 3D:
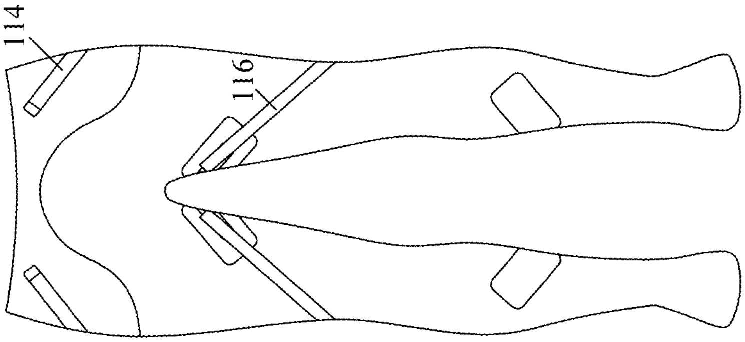
FIG. 3*d* is a front view of the leg garment of FIG. 3*a* having adjusted support elements.

FIG. 3*d* is a front view of the leg garment of FIG. 3*a* having adjusted support elements, according to an embodiment. Specifically, a distance in between the second ends of the first-pair support elements 114 and the first-pair sagitally mirrored anchor points 110 is reduced, and a distance in between the second ends of second-pair support elements 116 and the second-pair sagitally mirrored anchor points 112 is reduced.

Figure 3F:
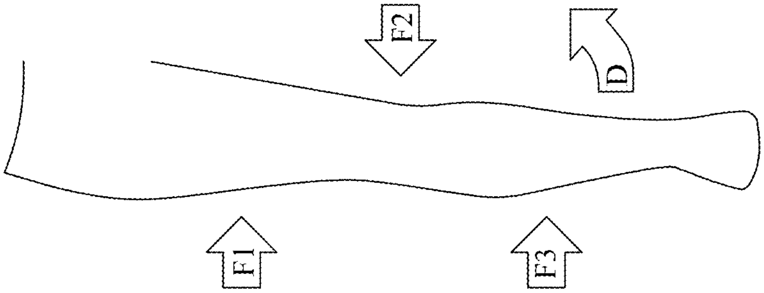
FIGS. 3*e*-3*f* show some of the forces imparted onto a right leg by the leg garment of FIG. 3*a*.
Figure 3E:
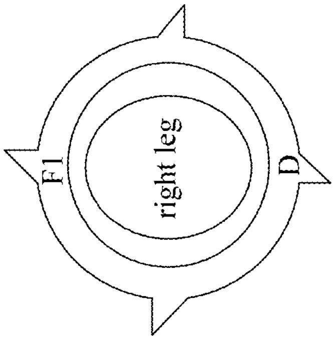

FIG. 3*e* is a top-down view of a right leg. Based on the path of the first-pair support elements 114 and the resistance to stretching of the first-pair support elements 114, stretching the first-pair support element on the right leg imparts an inwards torque F1 to the right leg, inducing internal hip rotation in direction D.

FIG. 3*f* is a front view of a right leg. Based on the path of the second-pair support elements 116 and the resistance to stretching of the second-pair support elements 116, stretching the second-pair support element on the right leg imparts forces F1 F2 F3 to the right leg, inducing a *varus*, inwards angulation of the lower leg in direction D. These forces reduce knee load and alleviate pain for wearers with osteoarthritis of the knee and provide knee rotational control.

Figure 4C:
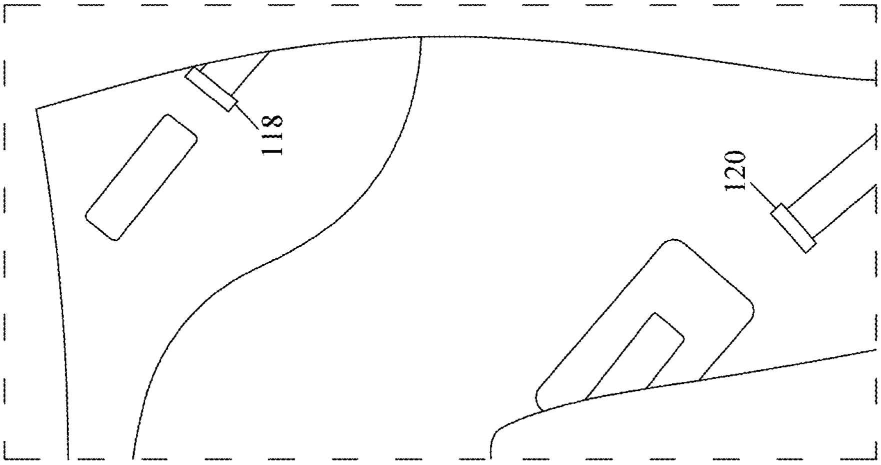
FIG. 4*c* is an enlarged fragmentary view of the leg garment of FIG. 4*a* having support elements caught by the catches.
Figure 4B:
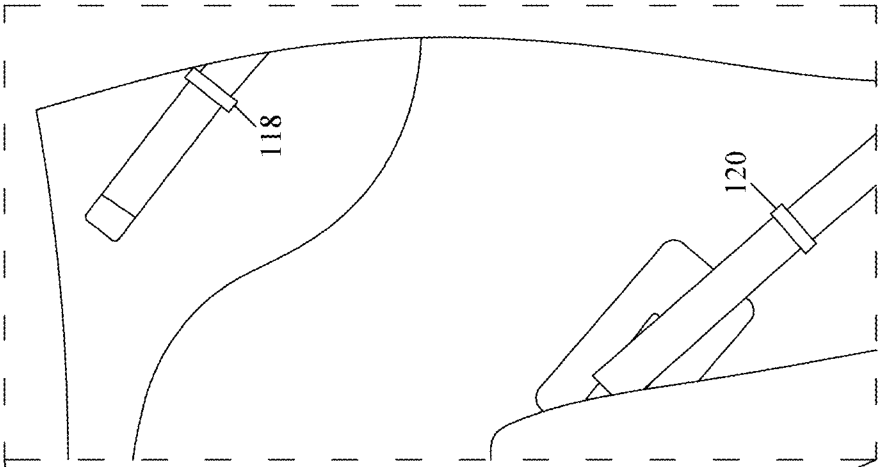
FIG. 4*b* is an enlarged fragmentary view of the leg garment of FIG. 4*a*.
Figure 4A:
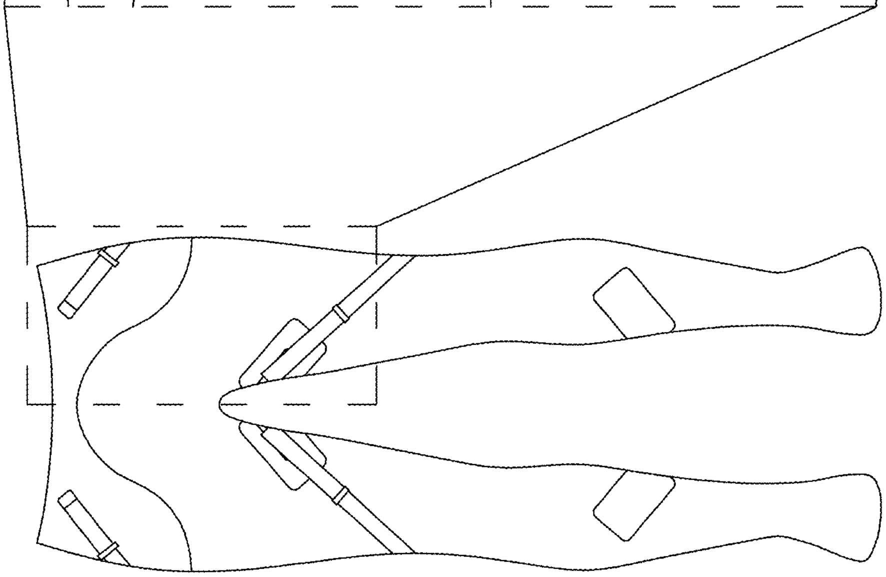
FIG. 4*a* is a front view of a leg garment with catches, according to an embodiment.

FIGS. 4*a*-4*b* show a leg garment 100 with catches, according to an embodiment. Specifically, FIG. 4*a* is a front view of the leg garment 100 and FIGS. 4*b*-4*c* are enlarged fragmentary views of the leg garment 100.

A first pair of catches 118 is positioned on a lateral portion of the hips. Alternatively, the first-pair catches 118 may be positioned along a path of the first-pair support elements 114 such that when the first-pair catches 118 catch second ends of the first-pair support elements 114, the tension of the first-pair support elements 114 is zero and the first-pair support elements 114 are taut. Yet alternatively, the first-pair catches 118 may be positioned along a path of the first-pair support elements 114 such that when the first-pair catches 118 catch second ends of the first-pair support elements 114, the tension of the first-pair support elements 114 is greater than zero.

A second pair of catches 120 is positioned on an anterior portion of the thighs. Alternatively, the second-pair catches 120 may be positioned along a path of the second-pair support elements 116 such that when the second-pair catches 120 catch second ends of the second-pair support elements 116, the tension of the second-pair support elements 116 is zero and the second-pair support elements 116 are taut. Yet alternatively, the second-pair catches 120 may be positioned along a path of the second-pair support elements 116 such that when the second-pair catches 120 catch second ends of the second-pair support elements 116, the tension of the second-pair support elements 116 is greater than zero.

The first-pair and second-pair catches comprise slot buckles holding first-pair and second-pair support elements. Second ends of the first-pair and second-pair support elements are thicker than the slots of the slot buckles such that second ends of the first-pair and second-pair support elements are caught by slot buckles when the first-pair and second-pair support elements are not attached to anchor points or when the first-pair and second-pair support elements are at a minimum tension. Alternatively, the first-pair and second-pair catches may comprise magnets or any other catch mechanisms that catch second ends of the first-pair and second-pair support elements when the first-pair and second-pair support elements are not attached to anchor points or when the first-pair and second-pair support elements are at a minimum tension.

Figure 5C:
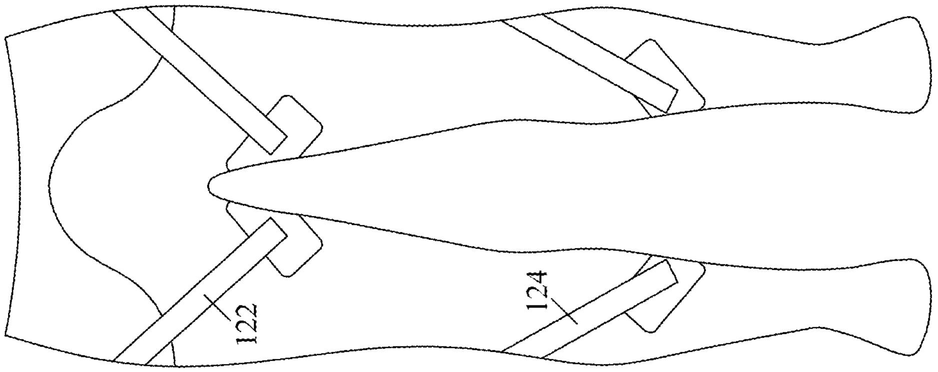
FIG. 5*c* is a back view of the leg garment of FIG. 5*a*.
Figure 5B:
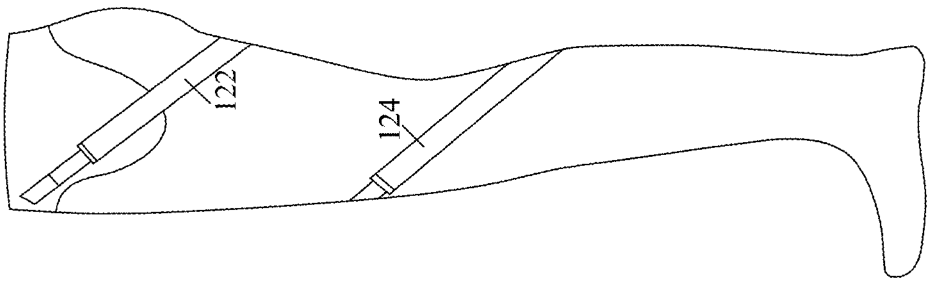
FIG. 5*b* is a right outside view of the leg garment of FIG. 5*a*.
Figure 5A:
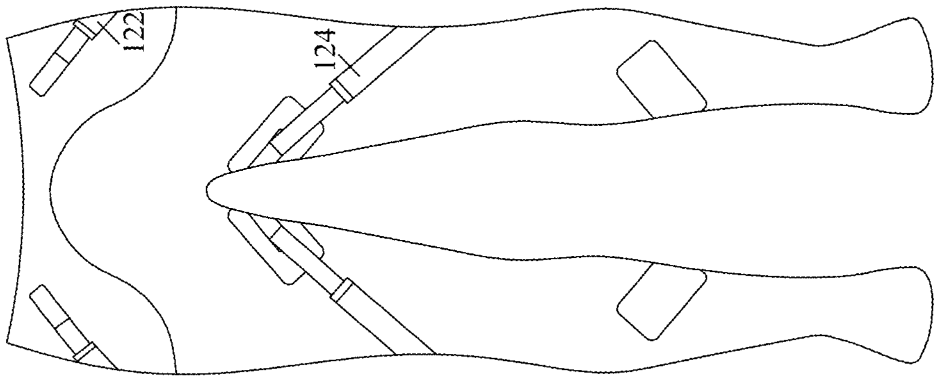
FIG. 5*a* is a front view of a leg garment with covers, according to an embodiment.

FIGS. 5*a*-5*c* show a leg garment 100 with covers, according to an embodiment. Specifically, FIG. 5*a* is front view of the leg garment 100, FIG. 5*b* is an outside right view of the leg garment 100, and FIG. 5*c* is a back view of the leg garment 100.

A first pair of covers extends 122 from first ends of the first-pair support elements 114 to the first-pair catches 118 such that the first-pair covers 122 enclose the first-pair support elements 114 and a portion of the base layer surrounding the first-pair support elements 114. Alternatively, the first-pair covers 122 may also enclose the first-pair catches 118. Yet alternatively, the first-pair covers extend 122 from first ends of the first-pair support elements 114 to first-pair sagitally mirrored anchor points 110 or first-pair tensioning mechanisms 126.

A second pair of covers extends 124 from first ends of the second-pair support elements 116 to the second-pair catches 120 such that the second-pair covers 124 enclose the second-pair support elements 116 and a portion of the base layer surrounding the second-pair support elements 116. Alternatively, the second-pair covers 124 may also enclose the first-pair catches 118. Yet alternatively, the second-pair covers extend 124 from first ends of the second-pair support elements 116 to second-pair sagitally mirrored anchor points 112 or second-pair tensioning mechanisms 128.

The first-pair and second-pair covers are weakly elastic such that the first-pair and second-pair covers weakly resist stretching under tensile forces. Preferred materials for the first-pair and second-pair covers include spandex or other weakly elastic materials. The first-pair and second-pair covers may be attached to the base layer 102 through sewing or adhesives, as well as through other common physical or chemical means known in the art.

The first-pair and second-pair covers have an appearance or design of the base layer 102 such that the first-pair and second-pair support elements are hidden, less the portion of the first-pair and second-pair support elements extending past the first-pair and second-pair catches.

Figure 6C:
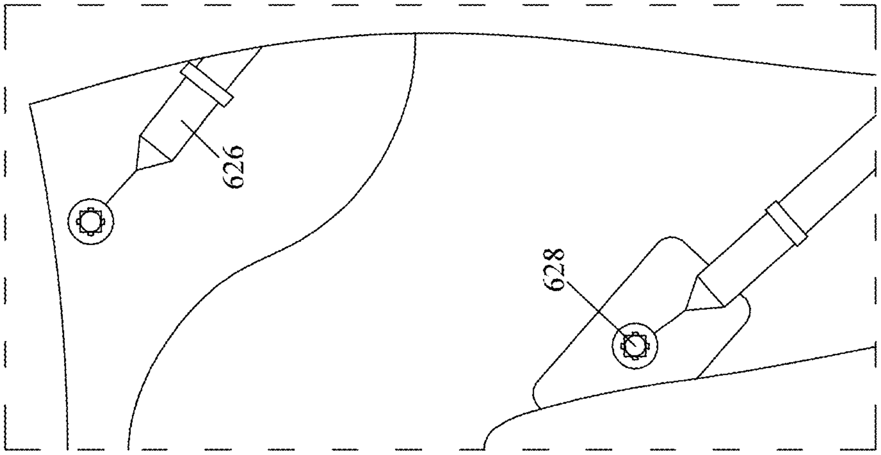
FIG. 6*c* is an enlarged fragmentary view of the leg garment of FIG. 6*a* having support elements tightened using the tensioning mechanisms.
Figure 6B:
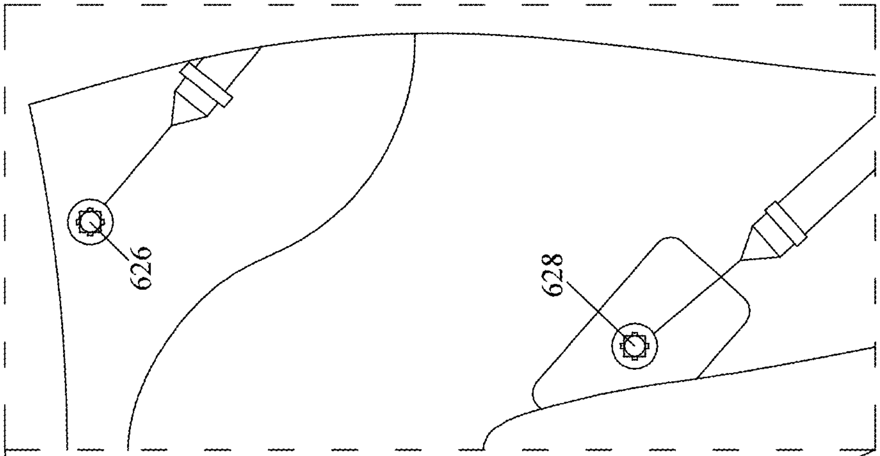
FIG. 6*b* is an enlarged fragmentary view of the leg garment of FIG. 6*a*.
Figure 6A:
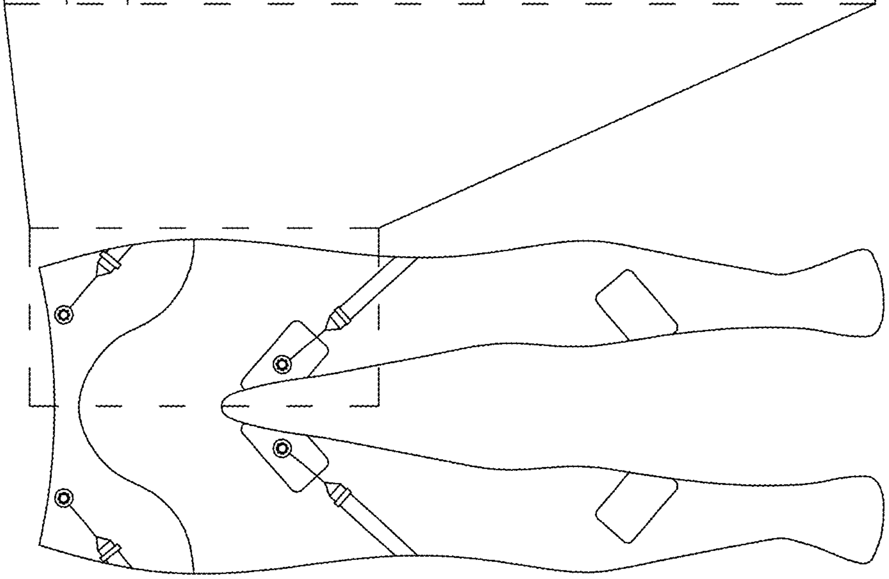
FIG. 6*a* is a front view of a leg garment with tensioning mechanisms, according to an embodiment.

FIGS. 6*a*-6*b* show a leg garment 100 with tensioning mechanisms, according to an embodiment. Specifically, FIG. 6*a* is a front view of the leg garment 100 and FIGS. 6*b*-6*c* are enlarged fragmentary views of the leg garment 100.

A first pair of tensioning mechanisms 126 are positioned on an anterior portion of the waist. Alternatively, the first-pair tensioning mechanisms 126 may be positioned on the waist. Yet alternatively, the first-pair tensioning mechanisms 126 may be positioned on reinforced portions of the base layer.

The second-pair tensioning mechanisms 128 are positioned on a medial-anterior portion of the thighs. Alternatively, the second-pair tensioning mechanisms 128 may be positioned on the thighs. Yet alternatively, the second-pair tensioning mechanisms 128 may be positioned on reinforced portions of the base layer.

The first-pair and second-pair tensioning mechanisms are BOA rotary dials. Cables are integrated into the BOA rotary dials and attached to second ends of the first-pair and second-pair support elements. Alternatively, the first-pair and second-pair tensioning mechanisms may be any mechanism that, when attached to second ends of the first-pair and second-pair support elements, can be used to tension the first-pair and second-pair support elements.

A desired tension of the first-pair support elements 114 is chosen by adjusting the first-pair tensioning mechanisms 126. For example, turning the BOA rotary dials clockwise pulls on the cables and tensions the first-pair support elements 114.

A desired tension of the second-pair support elements 116 is chosen by adjusting the second-pair tensioning mechanisms 128. For example, turning the BOA rotary dials clockwise pulls on the cables and tensions the second-pair support elements 116.

Figure 7C:
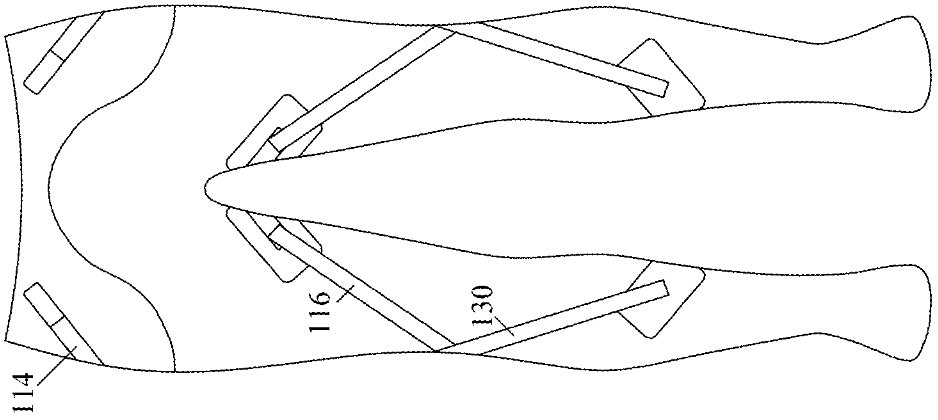
FIG. 7*b*-7*c* are, respectively, a right outside view and a back view of the leg garment of FIG. 7*a*.
Figure 7B:
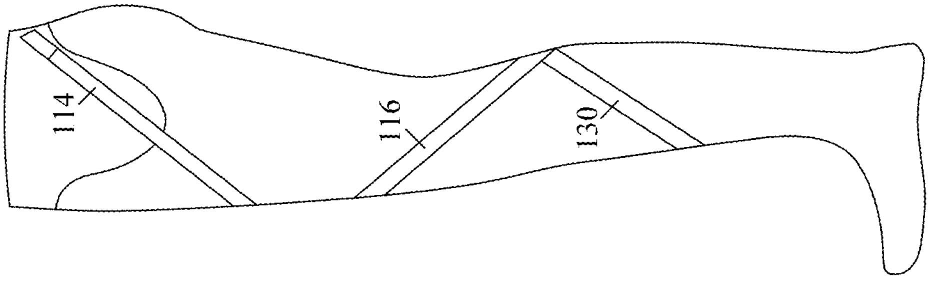
Figure 7A:
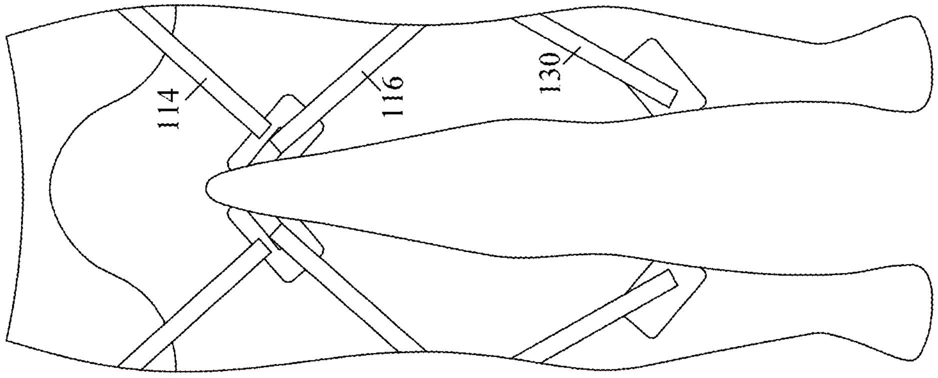
FIG. 7*a* is a front view of a leg garment with support elements, according to an embodiment.

FIGS. 7*a*-7*c* show a leg garment 100 with support elements, according to an embodiment. Specifically, FIG. 7*a* is front view of the leg garment 100, FIG. 7*b* is an outside right view of the leg garment 100, and FIG. 7*c* is a back view of the leg garment 100.

A first pair of support elements 114 each have first and second ends. The first end of each first-pair support element 114 is attached to the thigh portions 106. The second end of each first-pair support element 114 comprises a hook portion of a hook and loop fastener and attaches to one of the first-pair sagitally mirrored anchor points 110.

A path of each first-pair support element 114 starts on a medial portion of one of the thigh portions 706, spirals around a hip, and ends on a posterior portion of the hip portions 104. The first-pair support element 114 on the right leg spirals counter-clockwise and the first-pair support element 114 on the left leg spirals clockwise when viewed from above.

A second pair of support elements 116 each have first and second ends. The first end of each second-pair support element 116 is attached to one of the calf portions 108. The second end of each second-pair support element 116 comprises a hook portion of a hook and loop fastener and attaches to one of the second-pair sagitally mirrored anchor points 112.

A path of each second-pair support element 116 starts on a posterior-medial portion of one of the calf portions 108, spirals around a leg, and ends on an anterior-medial portion of one of the thigh portions 106. The second-pair support element 116 on the right leg spirals clockwise and the second-pair support element 116 on the left leg spirals counter-clockwise when viewed from above.

A third pair of support elements 130 each have first and second ends. The first end of each third-pair support element 130 is attached to one of the calf portions 108. The second end of each third-pair support element 130 comprises a hook portion of a hook and loop fastener and attaches to one of the medial-pair sagitally mirrored anchor points 132.

A path of each third-pair support element 130 starts on an anterior-medial portion of one of the calf portions 108, spirals around a leg, and ends on a posterior-medial portion of one of the thigh portions 106. The third-pair support element 130 on the right leg spirals clockwise and the second-pair support element 130 on the left leg spirals counter-clockwise when viewed from above.

Figure 7H:
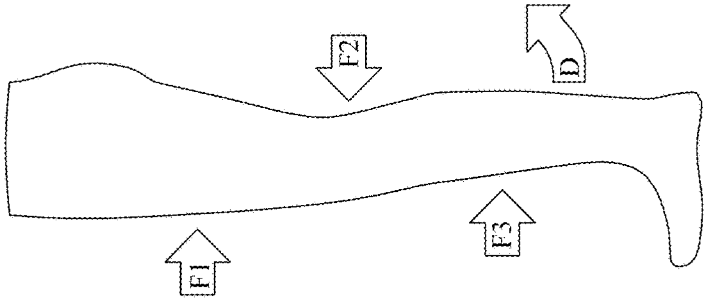
FIGS. 7*e*-7*h* show some of the forces imparted onto a right leg by the leg garment of FIG. 7*a*.
Figure 7G:
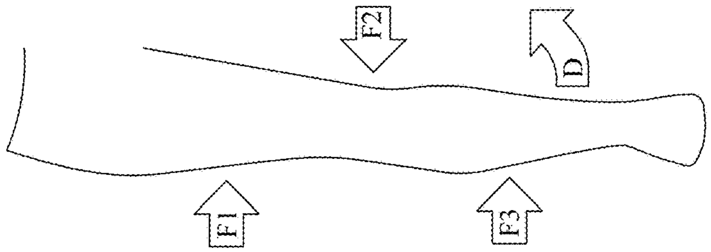
Figure 7F:
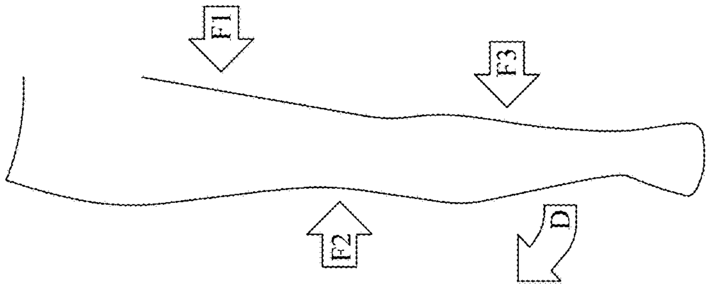
Figure 7E:
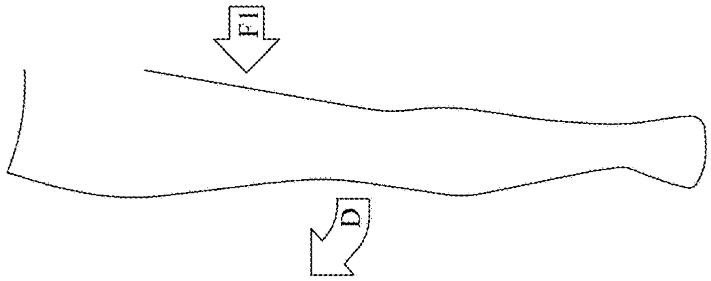
Figure 7D:
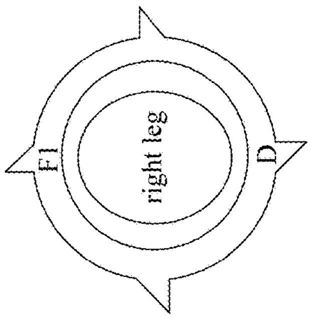
FIG. 7*d* is a top down view of the leg garment of FIG. 7*a*.

FIG. 7*d* is a top-down view of a right leg. Based on the path of the first-pair support elements 114 and the resistance to stretching of the first-pair support elements 114, stretching the first-pair support element on the right leg imparts an inwards torque F1 to the right leg, inducing internal hip rotation in direction D.

FIG. 7*e* is a front view of a right leg. Based on the path of the first-pair support elements 114 and the resistance to stretching of the second-pair support elements 114, stretching the second-pair support element on the right leg imparts a force F1 to the right leg, inducing leg abduction in direction D.

FIG. 7*f* is a front view of a right leg. Based on the path of the second-pair support elements 116 and the resistance to stretching of the second-pair support elements 114, stretching the second-pair support element on the right leg imparts forces F1 F2 F3 to the right leg, inducing a valgus, outwards angulation of the lower leg in direction D.

FIG. 7*g* is a front view of a right leg. Based on the path of the third-pair support elements 130 and the resistance to stretching of the third-pair support elements 130, stretching the third-pair support element on the right leg imparts forces F1 F2 F3 to the right leg, inducing leg abduction in direction D.

FIG. 7*h* is a left view of a right leg. Based on the path of the second-pair and third-pair support elements and the resistance to stretching of the second-pair and third-pair support elements, stretching the second-pair and third-pair support elements on the right leg imparts forces F1 F2 F3 to the right leg, inducing flexion of the lower leg in direction D.

These induced forces can drastically change the loading pattern at the hip and knee and may prevent pain due to patellal femoral pain syndrome, labrum tears, and OA pain of the knee and hip. Furthermore, the induced forces provide proprioceptive support as well as co-contraction that stabilizes the knee joint. Furthermore, these induced forces provide resistance to movement, requiring additional muscle engagement of the user at the knee and hip.

In some embodiments, the first-pair support elements 114 cross over the gluteus medius. When a wearer extends his or her hip, the quadriceps expand and the first-pair support elements 114 are stretched and tighten dynamically. Based on their configuration, when stretched during hip extension, the first-pair support elements' 114 resistance to stretching induces hip flexion.

In some embodiments, the first-pair support elements 114 cross over the gluteus maximus. When a wearer flexes his or her hips, the gluteus maximus expands and the first-pair support elements 114 are stretched and tighten dynamically. Based on their configuration, when stretched during hip flexion, the first-pair support elements' 114 resistance to stretching induces hip extension.

Figure 8C:
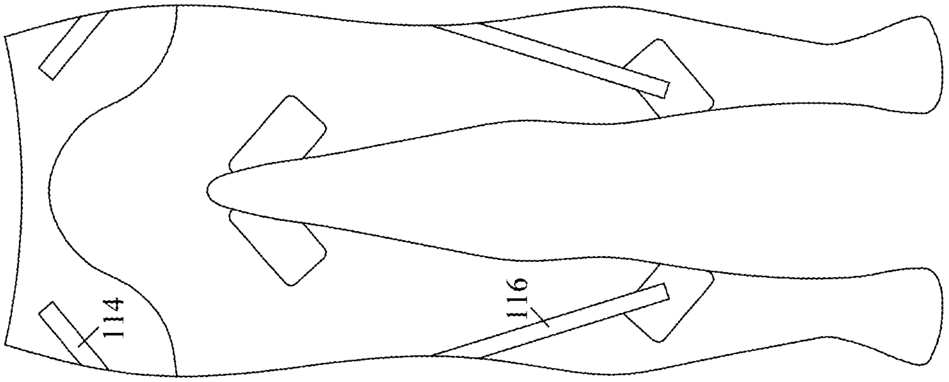
FIG. 8*c* is a back view of the leg garment of FIG. 8*a*.
Figure 8B:
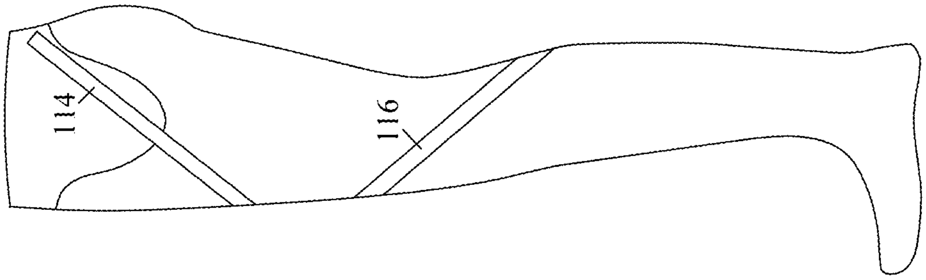
FIG. 8*b* is a right outside view of the leg garment of FIG. 8*a*.
Figure 8A:
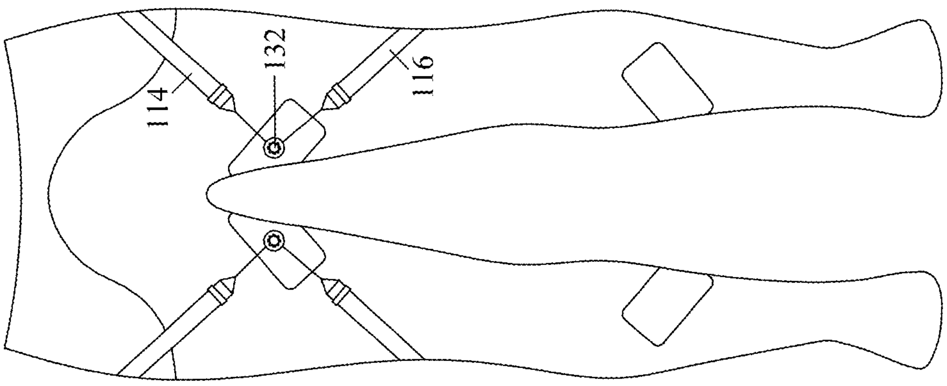
FIG. 8*a* is a front view of a leg garment with support elements and tensioning mechanisms, according to an embodiment.

FIGS. 8*a*-8*c* show a leg garment 100 with support elements and tensioning mechanisms, according to an embodiment. Specifically, FIG. 8*a* is front view of the leg garment 100, FIG. 8*b* is an outside right view of the leg garment 100, and FIG. 8*c* is a back view of the leg garment 100.

A medial pair of tensioning mechanisms 132 are positioned on a medial-anterior portion of the thighs. Alternatively, the medial-pair tensioning mechanisms 132 may be positioned on the thighs. Yet alternatively, the medial-pair tensioning mechanisms 132 may be positioned on reinforced portions of the base layer.

A desired tension of the first-pair support elements 114 and second-pair support elements 116 is chosen by adjusting the medial-pair tensioning mechanisms 142. For example, turning the BOA rotary dials clockwise pulls on the cables and tensions the first-pair support elements 114 and second-pair support elements 116.

Figure 9B:
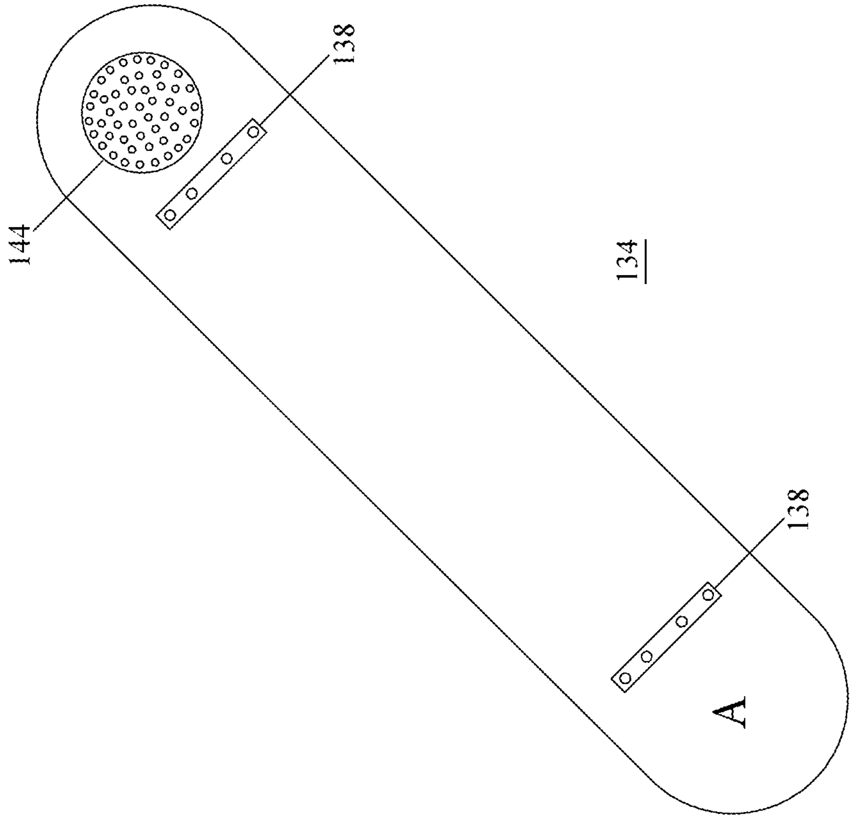
FIG. 9*b* is an inside view of the support element of FIG. 9*a*.
Figure 9A:
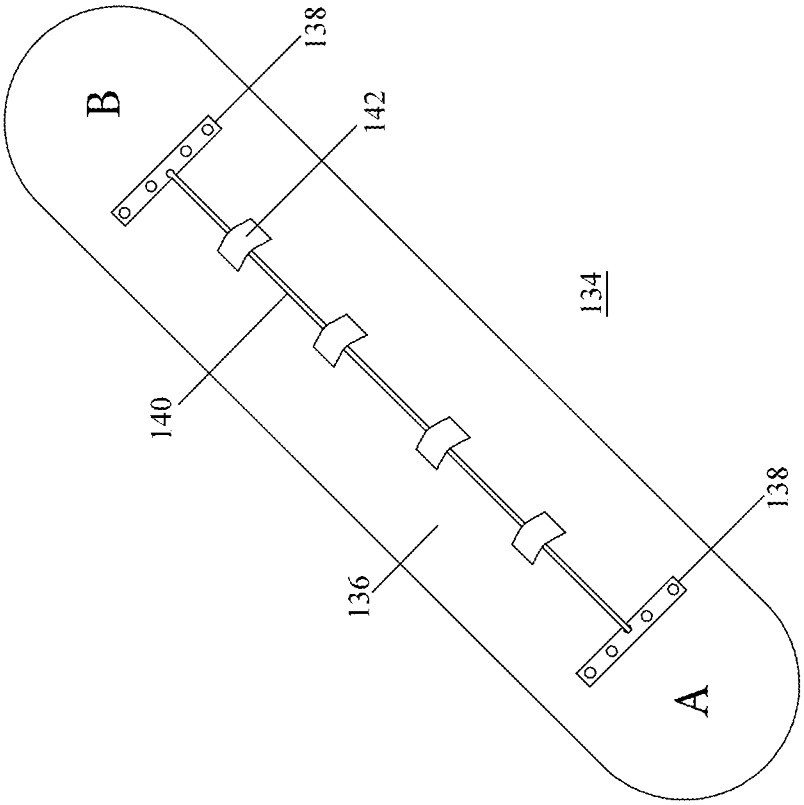
FIG. 9*a* is an outside view of a support element, according to an embodiment.

FIGS. 9*a*-9*b* show a support element 134, according to an embodiment. Specifically, FIG. 9*a* is an outside view of the support element 134 and FIG. 9*b* is an inside view of the support element 134. The outside of the support element 134 faces away from the surface of the leg garment 100 and the inside of the support element 134 faces towards the surface of the leg garment 100 during ordinary use.

A base 136 of the support element 134 is a flat stretch of rubber. Alternatively, the base 136 may be a flat stretch of spandex, nylon, or another elastic material.

The base 136 has a first end 'A' that is attached to a reinforced portion of the base layer 102 and a second end 'B' that attaches to an anchor point and/or tensioning mechanism.

The cable anchors 138 are comprised of two thin metal plates on opposite sides of the base 136 and coupled together using rivets. Small openings on a top portion of the cable anchors 138 secure ends of a cable 140. Alternatively, the cable anchors 138 may be any part or arrangement of parts attached to the base 136 that can hold ends of a cable 140. The cable anchors 138 may contact a large surface area of the base 136 to more evenly distribute tensive forces of the cable 140.

A cable 140 runs a length of the support element 134. Ends of the cable 140 are secured by the cable anchors 138. The cable 140 is inelastic. Alternatively, the cable 140 may be strongly elastic. The cable 140 limits the maximum stretch distance of support element 134 because the base 136 cannot be stretched much longer than the length of the cable 140 that runs through it.

In an embodiment, one end of the cable 140 may be integrated into a tensioning mechanism positioned on the support element 134 such that the tensioning mechanism is used to adjust a length of the cable 140.

At least one guide segment 142 is positioned in between the cable anchors 138. The guide segments 142 are semi-tubular portions of the base 136 that extend out from the base 136. Alternatively, the guide segments 142 may be a channel integrated into the base 136 along the length of the base 136.

An attachment surface 144 is positioned at the second end of the support element 134. The attachment surface is a hook portion of a hook and loop fastener and attaches to an anchor point with a corresponding loop portion of a hook and loop fastener. Alternatively, the attachment surface 144 comprises one part of any two-part fastening mechanism such as one part of a snap fastener or one part of a magnet pair.

Figure 10:
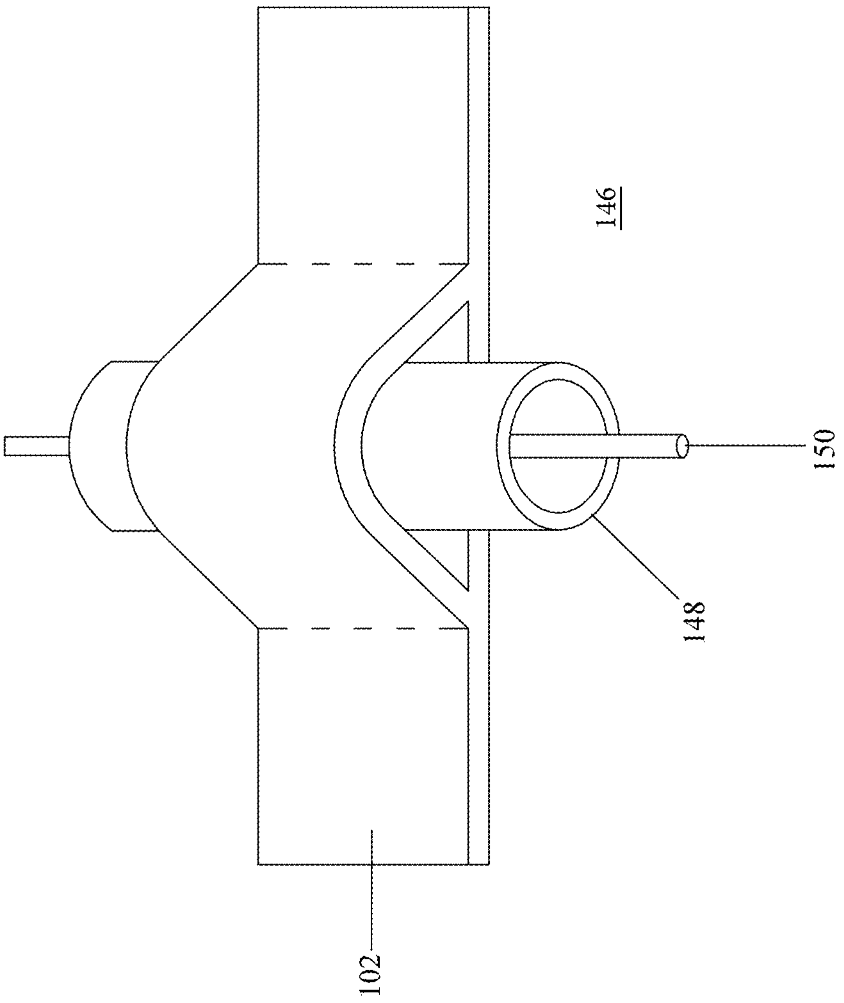
FIG. 10 is a cross-sectional top-front view of a cable system, according to an embodiment.

FIG. 10 is a cross-sectional top-front view of a cable system 146, according to an embodiment.

Channels 148 may be disposed within the base layer 102. The channels 148 have a circular cross-section. Alternately, the channels 148 have a rectangular cross section.

Cables 150 run through the channels 148. The cables 150 are inelastic. Alternatively, the cables 150 may be strongly elastic. The cables 150 may act as support elements.

In some embodiments, the portion of the base layer underneath the cables is reinforced.

In some embodiment, a plurality of cables may run parallel to each other. The plurality of parallel cables may be controlled by a single tensioning mechanism. Alternatively a first portion of the plurality of parallel cables is controlled by a first tensioning mechanism and a second portion of the plurality of parallel cables is controlled by a second tensioning mechanism.

Figure 11D:
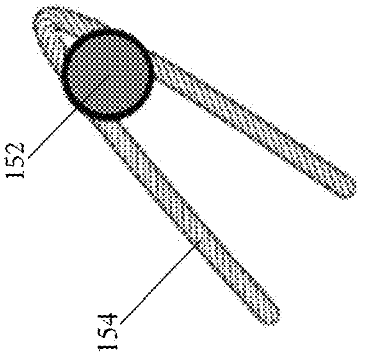
FIG. 11*d* is an enlarged view of a hook and bungee, according to an embodiment.
Figure 11C:
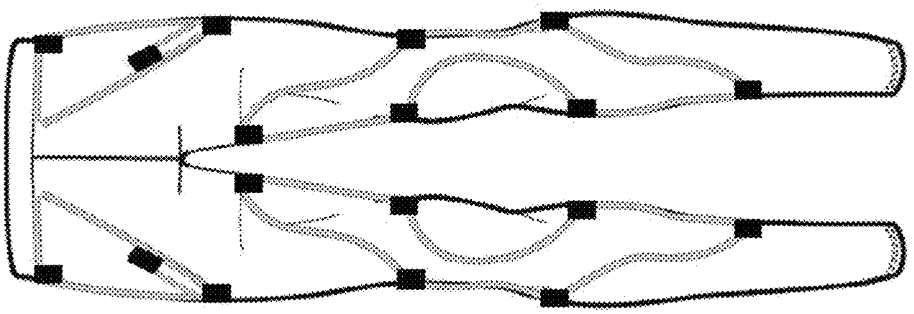
FIG. 11*c* is a back view of the leg garment of FIG. 11*a*.
Figure 11B:
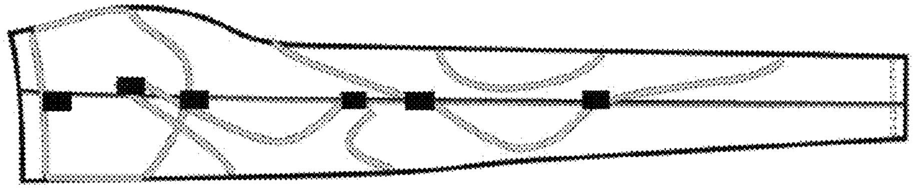
FIG. 11*b* is an outside right view of the leg garment of FIG. 11*a*.
Figure 11A:
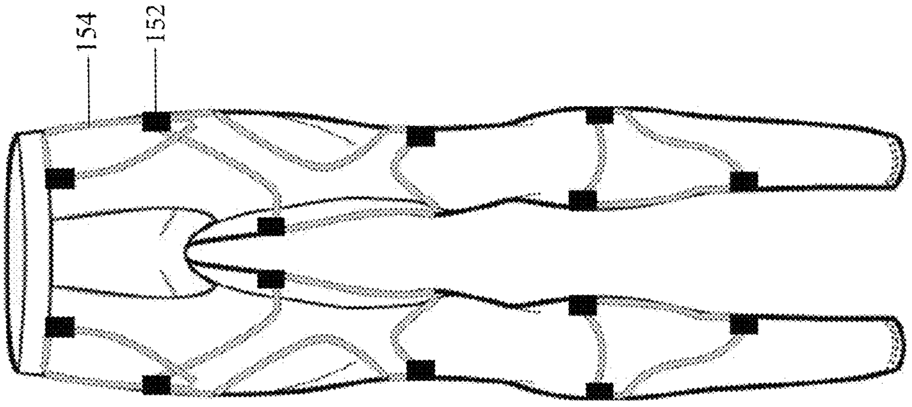
FIG. 11*a* is front view of the leg garment with hooks, according to an embodiment.

FIGS. 11*a*-11*c* show a leg garment 100 with hooks 152, according to an embodiment. Specifically, FIG. 11*a* is front view of the leg garment 100, FIG. 11*b* is an outside right view of the leg garment 100, and FIG. 11*c* is a back view of the leg garment 100.

Hooks 152 are strategically positioned throughout the leg garment 100 and are configured to removably secure support bungees 154.

A path of the bungees 154 spans, partially or entirely, across the leg garment. The bungees can be made tighter or looser by adjusting their paths. Where the bungees cross over different joins such as the hip, knew, or ankle, the tightness of the bungees becomes dynamic.

In some embodiments, pressure reduction panels are placed below the bungees to more evenly distribute pressure across the leg garment 100.

FIG. 11*d* is an enlarged view of a hook 152 and bungee 154.

In some embodiments, the leg garments may have a tightening band around the waist that keeps the leg garment in place during wear.

In some embodiments, the first ends of the support elements are detachable from the base layer 102, permitting the support elements to be interchangeable. A wearer can swap out a support element for a new support element that has different properties. For example, a wearer can swap to a new support element that is thicker. The increased thickness of the new support element would increase the support element's resistance to being stretched so a wearer using the new support element would not have to move his or her leg as far and/or tighten the tensioning mechanisms in order to induce the desired motion. Thus, the support elements may be customized to achieve the desired reaction.

In some embodiments, a support element may be segmented into a plurality of shorter segments, where the ends of the shorter segments are anchored to the garment and each support element may be separately adjustable with its own tensioning mechanism. The shorter support element segments would respond separately to some motions or tensioning with the tensioning mechanism when compared with the original, unsegmented support element.

In some embodiment, support elements that travel along the same extended path may be combined into one longer support element where adjacent ends of the original support elements are linked together. The longer support elements would respond together to some motions or tensioning with the tensioning mechanism when compared with the original, uncombined support elements.

In some embodiments, conductive fibers are disposed within the leg garment at strategic locations, providing heat therapy when the conductive fibers are connected to a power source such as a battery pack.

In some embodiments, arrays of flexible peltier plates are disposed within the leg garment at strategic locations, providing cold therapy when the arrays are connected to a power source such as a battery pack.

In some embodiments, sensors are disposed within the leg garment at strategic locations. For example, but not limited to, step counters, full knee extension sensors (which measure when you reach full knee extension—a motion often limited when knee pain reduces quad activation), quad muscle activation sensors (to determine the extent of therapy needed), and/or tension sensors that track how often a motion is performed.

In some embodiments, data collected by these sensors is displayed in an application. A user could see how many calories he or she burned, how many pounds he or she has engaged with, how close he or she is to reaching full extension and a more normal gait.

We claim:

1. A leg garment comprising:

a base layer is configured to extend down from a waist, wherein two hip portions, two medial thigh portions, and two calf portions of the base layer are reinforced to have increased resistance to stretching;

a first pair of sagitally mirrored anchor points are positioned on one of the hip portions;

a second pair of sagitally mirrored anchor points are positioned on one of the medial thigh portions;

a third pair of sagitally mirrored anchor points are positioned on one of the calf portions;

a first support element, wherein a first end of the first support element is attached to one of the first pair of sagitally mirrored anchor points;

a second end of the first support element attaches to one of the second pair of sagitally mirrored anchor points;

a path of the first support element spans from one of the hip portions to one of the medial thigh portions and is configured to spiral around a hip; and a second support element, wherein a first end of the second support element is attached to one of the second pair of sagitally mirrored anchor points;

a second end of the second support element attaches to one of the third pair of sagitally mirrored anchor points; and a path of the second support element spans from one of the medial thigh portions to one of the calf portions and is configured to spiral around a leg.

2. The leg garment of claim 1, further comprising a first catch positioned along the path of the first support element and configured to catch the second end of the first support element when the first support element is not attached to one of the first pair of sagitally mirrored anchor points or when the first support element is at a minimum tension; and a second catch positioned along the path of the second support element and configured to catch the second end of the second support element when the second support element is not attached to one of the second-pair of sagitally mirrored anchor points or when the second support element is at a minimum tension.

3. The leg garment of claim 2, further comprising a first cover extending from the first end of the first support element to the first catch, the first cover enclosing the first support element and a portion of the base layer surrounding the first support element; and a second cover extending from the first end of the second support element to the second catch, the second strap cover enclosing the second support element and a portion of the base layer surrounding the second support element.

4. The leg garment of claim 1, wherein a desired tension of the first support element is selected by adjusting a distance in between the second end of the first support element and one of the first-pair of sagitally mirrored anchor points; and a desired tension of the second support element is selected by adjusting a distance in between the second end of the second support element and one of the second-pair of sagitally mirrored anchor points.

5. The leg garment of claim 4, wherein, based on the path of the first support element and a resistance to stretching of the first support element, stretching the first support element is configured to induce internal hip rotation.

6. The leg garment of claim 4, wherein, based on the path of the first support element and a resistance to stretching of the first support element, stretching the first support element is configured to induce external hip rotation and resists internal hip rotation.

7. The leg garment of claim 4, wherein the first support element comprises one of a strongly elastic cable and an inelastic cable running a length of the first support element; and the second support element comprises one of a strongly elastic cable and an inelastic cable running a length of the second support element.

8. The leg garment of claim 4, further comprising a third support element, wherein a first end of the third support element is attached to the second pair of sagitally mirrored anchor points;

a second end of the third support element attaches to one of the third pair of sagitally mirrored anchor points;

a path of the third support element spans from one of the medial thigh portions to one of the calf portions and spirals around a leg.

9. The leg garment of claim 1, wherein the first pair of sagitally mirrored anchor points further include first tensioning mechanisms;

the second pair of sagitally mirrored anchor points further include second tensioning mechanisms;

a desired tension of the first support element is selected by adjusting one of the first tensioning mechanisms; and a desired tension of the second support element is selected by adjusting one of the second tensioning mechanisms.

10. The leg garment of claim 9, wherein at least one of the first tensioning mechanisms and the second tensioning mechanisms is enclosed within the cover.

11. The leg garment of claim 9, wherein the path of the first support element is configured to cross over a gluteus medius such that, based on the path of the first support element and a resistance to stretching of the first support element, stretching the first support element induces hip flexion and resists hip extension.

12. The leg garment of claim 9, wherein the path of the first support element is configured to cross over a gluteus maximus such that, based on the path of the first support element and a resistance to stretching of the first support element, stretching the first support element induces hip extension and resists hip flexion.

13. The leg garment of claim 9, wherein the path of the second support element is such that, based on the path of the second support element and a resistance to stretching of the second support element, stretching the second support element is configured to induce internal knee rotation and knee flexion, and resists knee extension.

14. The leg garment of claim 9, wherein the path of the second support element is such that, based on the path of the second support element and a resistance to stretching of the second support element, stretching the second support element is configured to induce external knee rotation and knee flexion, and resists knee extension.

15. The leg garment of claim 1, the second end of the first support element and the first end of the second support elements attach to one of the second pair of sagitally mirrored anchor points; and a desired tension of the first and second support element is selected by adjusting distances in between the second end of the first support element and the first end of the second support elements and the one of the second pair of sagitally mirrored anchor points.

16. The leg garment of claim 15, the second pair of sagitally mirrored anchor points are tensioning mechanisms; and a desired tension of the first and second support elements is selected by adjusting one of the tensioning mechanisms.

17. A leg garment comprising:

a base layer is configured to extend down from a waist, wherein a hip portion, medial thigh portions, and calf portions of the base layer are reinforced to have increased resistance to stretching;

a first pair of sagitally mirrored anchor points positioned on the hip portion;

a second pair of sagitally mirrored anchor points positioned on one of the medial thigh portions;

a third pair of sagitally mirrored anchor points positioned on one of the calf portions;

a first support element, wherein a first end of the first support element is attached to one of the first pair of sagitally mirrored anchor points;

a second end of the first support element attaches to one of the second pair of sagitally mirrored anchor points;

a path of the first support element spans from one of the hip portions to one of the medial thigh portions and is configured to spiral around a hip;

a second support element, wherein a first end of the second support element is attached to one of the second pair of sagitally mirrored anchor points;

a second end of the second support element attaches to one of the third pair of sagitally mirrored anchor points;

a path of the second support element spans from one of the medial thigh portions to one of the calf portions and is configured to spiral around a leg;

a first catch positioned along the path of the first support element and configured to catch the second end of the first support element when the first support element is not attached to one of the first pair of sagitally mirrored anchor points or when the first support element is at a minimum tension; and a second catch positioned along the path of the second support element and configured to catch the second end of the second support element when the second support element is not attached to one of the second pair of sagitally mirrored anchor points or when the second support element is at a minimum tension.

18. The leg garment of claim 17, further comprising a first cover extending from the first end of the first support element to the first catch, the first cover enclosing the first support element and a portion of the base layer surrounding the first support element; and a second cover extending from the first end of the second support element to the second catch, the second strap cover enclosing the second support element and a portion of the base layer surrounding the second support element.

19. The leg garment of claim 17, wherein a desired tension of the first support element is selected by adjusting a distance in between the second end of the first support element and one of the first pair of sagitally mirrored anchor points; and a desired tension of the second support element is selected by adjusting a distance in between the second end of the second support element and one of the second pair of sagitally mirrored anchor points.

20. The leg garment of claim 17, wherein the distance in between the second end of the first support element and one of the first pair of sagitally mirrored anchor points is adjusted using a first tensioning mechanism; and the distance in between the second end of the second support element and one of the second pair of sagitally mirrored anchor points is adjusted using a second tensioning mechanism.

21. The leg garment of claim 17 wherein the path of the first support element spirals in a clockwise direction and the path of the second support element spirals in a counter-clockwise direction.

* * * * *